United States Patent [19]

Ansari et al.

[11] 4,311,617
[45] Jan. 19, 1982

[54] PERFUMERY COMPOSITIONS

[75] Inventors: Hifzur R. Ansari, Rayleigh; Benjamin O. Isaac, Ilford; Horst R. Wagner, Woodford Green, all of England

[73] Assignee: Bush Boake Allen Limited, London, England

[21] Appl. No.: 162,326

[22] Filed: Jun. 24, 1980

Related U.S. Application Data

[63] Continuation of Ser. No. 915,126, Jun. 13, 1978, abandoned, which is a continuation of Ser. No. 810,044, Jun. 27, 1977, abandoned, which is a continuation of Ser. No. 689,377, May 24, 1976, abandoned.

[30] Foreign Application Priority Data

May 29, 1975 [GB] United Kingdom ............... 23413/75

[51] Int. Cl.³ .................................................. A61K 7/46
[52] U.S. Cl. ................................ 252/522 R; 568/496; 568/678
[58] Field of Search ................... 252/522 R; 568/496

[56] References Cited

U.S. PATENT DOCUMENTS 3,519,681 7/1970 Sancy ................................... 568/496
3,904,662 9/1975 Henrick et al. ..................... 424/312
3,919,324 11/1975 Himmele et al. ................... 568/496
3,959,396 5/1976 Ochsher et al. ..................... 568/465
3,978,135 8/1976 Charbardes ......................... 568/465

FOREIGN PATENT DOCUMENTS 859567 1/1961 United Kingdom ............ 252/522 R

Primary Examiner—John F. Niebling
Attorney, Agent, or Firm—Frishauf, Holtz, Goodman & Woodward

[57] ABSTRACT

Compounds having the general formula

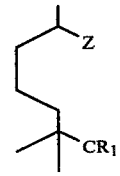

wherein $R_1$ represents a hydrogen atom or an alkyl group having from 1 to 4 carbon atoms and Z represents a formyl group —CHO or a hydroxyl group or a group $OR_1$ wherein $R_2$ represents an acyl group having from 1 to 6 carbon atoms, have been discovered to possess attractive fruity-floral odors. They are useful as ingredients of compounded perfumery compositions.

7 Claims, No Drawings

PERFUMERY COMPOSITIONS

This is a continuation of application Ser. No. 915,126, filed June 13, 1978, abandoned, which, in turn, is a continuation of Ser. No. 810,044, filed June 27, 1977 (now abandoned), which, in turn is a continuation of Ser. No. 689,377 filed May 24, 1976 (now abandoned).

This invention relates to certain novel chemicals which are of use in the perfumery industry, to methods for their preparation and to certain novel chemicals formed as intemediates in these preparations. The invention also relates to compounded perfumery compositions of the type where a number of odoriferous ingredients of synthetic or natural origin are admixed or compounded to form a perfumery concentrate. Such concentrates may find use as such or after dilution but more usually they are added in small proportions to other materials such as to space sprays or to soap, detergents, cosmetic or deodorant compositions or to substrates such as fabrics, fibres or paper products, in order to provide them with agreeable olfactory properties. Thus such concentrates are products of commerce and the perfumery concentrates may comprise a simple or complex mixture of individual perfumery compounds.

From one aspect the invention provides novel chemicals having the formula I

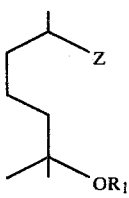

wherein $R_1$ represents a hydrogen atom or an alkyl group having from 1 to 4 carbon atoms and Z represent a formyl group —CHO or a primary alcohol group —$CH_2OH$ or a group $CH_2OR_2$ wherein $R_2$ is an acyl group having from 1 to 6 carbon atoms. Such compounds may be individual optical isomers or a mixture of these individual optical isomers. The aldehydes may be designated hydroxy (or alkoxy) melonals and the alcohols hydroxy or alkoxy melonols. Such a nomenclature will be adopted for the purposes of this disclosure.

The novel compounds having said formula I are also conveniently designated by having Z defined as the group —$CH(H)_mOR_m$ wherein m is 0 or 1, and R is selected from the group consisting of hydrogen, and acyl groups derived from a carboxylic acid having from 1 to 6 carbon atoms. It has been discovered that these compounds possess a marked fruity-floral type of odour. They exhibit, to varying degrees, a perceptible melon odour together with a floral note reminiscent of muguet or lily of the valley. These two notes blend harmoniously resulting in the novel compounds having particularly attractive odours. The relative intensity of the two notes varies with the particular compound and accordingly when formulating a compounded perfumery composition the selection of an appropriate compound will enable the perfumer to bring the desired note to prominence.

It has been discovered that the novel compounds of the above formula are suited for blending with a wide range of odoriferous chemicals so as to produce a compounded perfumery composition. The novel aldehydes of the invention i.e. those compounds having one of the above formulae wherein Z represents a formyl group are especially valuable for present use. Especially preferred as an ingredient of a compounded perfumery composition is the aldehyde wherein R represents a methyl group; i.e. 6-methoxy-2,6-dimethylheptanal.

In general these novel compounds wherein Z represents a hydroxyl group have less powerful aromas than the corresponding aldehydes and are therefore, in general, less preferred for use as ingredients of compounded perfumery compositions. We have discovered that a mixture of any of the novel aldehydes of our invention with a novel alcohol of the invention possesses an extremely attractive odour which has slightly more body than either used alone. Preferably any particular aldehyde will be admixed with the corresponding alcohol in order to maximise this complementary odour effect.

Thus while our invention includes the use of mixtures of any of the novel compounds defined above as ingredients of compounded perfumery compositions, mixtures of a melonol with the corresponding melonal are particularly preferred. Such mixtures may comprise two or more ingredients in any proportion but preferably they will comprise at least 25%, preferably 50% and most preferably 75% by weight of one or more aldehydes in admixture with the corresponding alcohols.

The novel perfumery compositions may be compounded according to recognised techniques of perfumery employing known odoriferous perfumery ingredients, e.g. techniques and ingredients mentioned in the standard text books "Soap, Perfumery and Cosmetics" by W. A. Poucher, 7th Edition, published by Chapman & Hall (London) 1959; "Perfume and Flavour Chemicals" by S. Arctander, published by the author (Montclair) 1959 and "Perfume and Flavour Materials of Natural Origin" also by S. Arctander, self-published, Elizabeth, N.J., 1960. The relevant disclosures of the aforesaid text books are hereby incorporated by reference herein. Specific odoriferous ingredients which may be blended with the novel compounds of this invention include the 2,6 dimethyl 2 alkoxy octan-7-ols, vetivert oil, vetiverol, vetiveryl acetate, guaiac wood oil, guaiac wood acetate, coumarin, musk ketone, lauric aldehyde, benzyl acetate, dimethyl benzyl carbinol, dimethyl benzyl carbinyl acetate, rose absolute, jasmin absolute, ionones, iso-nonyl acetate, methyl phenyl acetate, styrallyl acetate, β-phenyl ethanol, citronellol, citronellal, hydroxy citronellal, geranium oil, geraniol, linalol, bornol, lavandin oil, linalyl acetate, patchouli oil, petitgrain oil, bergamot oil, heliotropin, ethylene brassylate, undecyl aldehyde, cinnamaldehyde, benzyl salicylate, cinnamyl alcohol, clove bud oil, bay oil, nutmeg oil, pimento berry oil, terpineol, ylang oil, benzyl benzoate, sandalwood oil, clary sage oil, amyl salicylate, labdanum resin, methyl ionones, dihydromyrcenol, orange oil, vanillin, ethylvanillin, olibanum resin, musk ambrette, rhodinol, mandarin oil, methyl nonyl acetaldehyde, neroli oil, cedrol, oakmoss, isovalanone, eugenol, iso-eugenol, cedarwood oil, p-tert-butyl cyclohexyl acetate.

Particularly preferred odoriferous ingredients for blending with the novel compounds of the invention are linalool, citronellol, geraniol, phenylethyl alcohol, terpineol, hydroxycitronellal, and methoxycitronellal.

It has been found that these compounds have a high degree of utility in perfumery compositions in the capacity of odoriferous ingredients. They can be employed either individually or as mixtures of two or more compounds, in a wide variety of proportions say from 0.1 to 55 parts by weight of the compounded perfumery compositions. In some cases it may be desirable to employ the novel compounds of the invention in a proportion of from 0.1 to 20 parts by weight and in others in a proportion of from 5.0 to 50 parts by weight.

The novel compounds of the invention are conveniently obtained from $C_{10}$ terpene compounds such as are widely used in the perfumery industry. The synthesis of the aldehydes of formula I proceeds through a series of intermediates having $C_{10}$ skeletons, certain of which are believed to be novel and constitute a further aspect of the invention.

A convenient group of starting materials for this synthesis the 2-substituted citronellenes i.e. the 2-alkoxy (or hydroxy)-2,6, dimethyl-octa-7enes of the formula

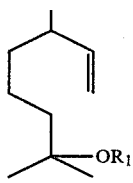

wherein R represents a hydrogen atom or an alkyl group having from 1 to 4 carbon atoms. The preparation of these compounds from 2,6-dimethyl-2,7 octadiene is described in British Pat. No. 859568. Treatment of the 2-substituted compounds with a per acid derived from a lower carboxylic acid such as performic acid at a temperature of 50°–60° C. results of the formation of the corresponding diols having the formula

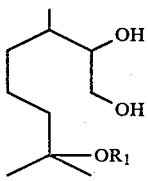

among other products. This reaction is well known in the art of synthetic organic chemistry and is described in the relevant text books. Conveniently the olefin is dissolved in formic acid and hydrogen peroxide solution is added so as to generate per formic acid in situ. The diol is generated at least partially in the form of its formate ester which is preferably hydrolysed before separation of the diol from the product mixture which may be achieved by using conventional techniques such as fractional distillation.

The vicinal diol is then converted to the corresponding ketoalcohol by oxidation. This conversion may be carried out using catalytic dehydrogenation, preferably employing copper chromite as the dehydrogenation catalyst. The dehydrogenation is carried out at temperatures in the range 150° to 200° C., preferably 160° to 180° C. The product is a keto-alcohol having the formula

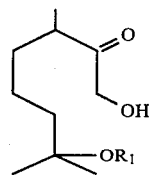

wherein $R_1$ is as hereinbefore defined. Such compounds are believed to be novel and constitute a further aspect of our invention.

We have discovered that these novel compounds which contain 10 carbon atoms as part of their skeletal structure may be converted to the desired novel compounds of the invention by the action of a basic material. Accordingly from a further aspect our invention comprises processes for the preparation of a compound having the formula

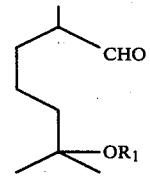

which comprise treatment of a compound having the formula

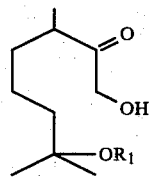

with a basic material.

This basification may be achieved by addition of an aqueous solution of a base such as potassium or sodium hydroxide, sodium carbonate or sodium bicarbonate. Alternatively the basification may be carried out under anhydrous conditions using a suspension of a suitable base e.g. potassium or sodium carbonate in a suitable inert non-aqueous solvent. Also if desired an organic base such as pyridine or other organic amines may be employed. The base is preferably added in a quantity of from 1 to 20%, more preferably 2 to 10% by weight of the the keto-alcohol. Aqueous solutions of water-soluble bases may conveniently be empolyed in a quantity approximately equal to the weight of keto-alcohol used. The reaction is preferably carried out at temperatures in the range 20° to 100° C. The desired product is conveniently removed continuously by distillation.

Alternatively the vicinal diols of the formula

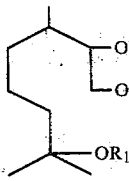

may be converted directly to the corresponding aldehyde by treating them with those oxidising agents known in the art of synthetic organic chemistry for the ability to cleave vicinal diols so as to produce aldehydes e.g. lead tetra-acetate and periodic acid. Other oxidising agents which can be used in order to effect this conversion but whose use is less preferred include potassium permanganate, manganese dioxide and chromic acid. The reaction is preferably carried out in a non-polar organic solvent. Care should be taken to minimise the further oxidation of the desired aldehyde to the corresponding carboxylic acid; conveniently the aldehyde is continuously distilled out of the reaction vessel.

We have also discovered a novel procedure by which the $C_{10}$ vicinal diols described above may be converted to a mixture of the desired $C_9$ alcohols and aldehydes. This process is one of heating the diol under anhydrous conditions in the presence of a strong base such as an alkali metal hydroxide, carbonate, or bicarbonate. Conveniently from 1 to 10%, preferably 2 to 6% by weight of the dry solid base is added to the diol and the mixture heated to a temperature in the range 250° to 275° C. The reaction product comprises a mixture of the corresponding desired alcohol and aldehyde in which the alcohol usually predominates. As described above this mixture may itself find use as an ingredient of a compounded perfumery composition or alternatively the mixture may be only partially separated so as to produce a mixture of aldehyde and alcohol in which the aldehyde predominates.

The novel aldehydes, alcohols and carboxylic acid esters of the invention may be interconverted as desired using the standard techniques of synthetic organic chemistry. The alcohols are conveniently obtained from the corresponding aldehydes by a process of reduction. Reduction with a metal hydride such as sodium borohydride is especially useful.

The carboxylic acid esters are prepared from the appropriate alcohol by treatment with a stoichiometric quantity of a suitable esterifying agent such as a carboxylic acid or a carboxylic acid anhydride.

The invention is illustrated by the following examples:

EXAMPLE 1

Preparation of 7-Methoxy-3,7-dimethyl-2-Keto-Octanol

7-Methoxy-3,7-dimethyl octan-1,2-diol (203 g) was dehydrogenated at 170° C. in the presence of Copper Chromite (10 g) to give the Keto-alcohol (175 g: 87% yield), bP 85°–88° C. at 0.1 mm, $\alpha(20/D)+1.7$ (C 3.52 in MeOH).

EXAMPLE 2

Preparation of 6-Methoxy-2,6-dimethylheptanal (i) Aqueous potassium hydroxide

The above Keto-alcohol (40 g) was stirred with a 5% solution of potassium hydroxide at 35°–40° C. for a period of 2 hours. Work up by washing with water and extracting the product with ether gave methoxymelonal (4 g), bP 50–52 at 0.5 mm.

(ii) Anhydrous Potassium Carbonate

The Keto-alcohol (40 g) and anhydrous potassim carbonate (1 g) was heated while distilling the product formed between 50°–62° C. under reduced pressure of 0.5–1 mm. Final fractionation of the distillate gave the pure aldehyde (6.5 g).

(iii) Periodate Oxidation

7-Methoxy-3,7-dimethyl octan-1,2-diol (40 g) was treated with periodic acid in tetrahydrofuren; work up with water followed by diluted sodium bicarbonate wash gave the aldehyde (10 g) with specific rotating $\alpha(22/D+13.69.$

EXAMPLE 3

Preparation of a mixture of Hydroxymelonal and Hydroxymelanol 188.0 gms of 7-hydroxy-3,7-dimethyl-octan-1,2-diol were heated with 10 gm of sodium hydroxide at a temperature of 250° C. The desired cleavage product was continuously removed by distillation. After 6 hours 90 gm of product had collected which comprised a mixture of 4 parts of 6-hydroxy-2,6-dimethylheptanol and 1 part of the corresponding aldehyde. This mixture was dehydrogenated by passing it over a copper chromite catalyst at a temperature of 180° to 200° C. The product 6-hydroxy-2,6-dimethylheptanal had a powerful lily of the valey type odour. Its boiling point was 94° C./1 cm and its IR spectrum showed prominent peaks at 3430, 2715, 1723, 1465, 1350, 1215, 1160, 930 and 910 cm$^{-1}$.

EXAMPLE 6

A compounded perfumery composition having a muguet type odour was made up as follows:

| (all proportions are parts by weight) | |
|---|---|
| Phenylacetaldehyde (10%) | 15 |
| Cis hexenylacetate (10%) | 10 |
| Benzyl acetate | 15 |
| Styrax oil | 20 |
| Anisaldehyde | 5 |
| Methylisoeugenol | 60 |
| Benzyl Salicylate | 40 |
| Hedione | 20 |
| Jasmin absolute | 1 |
| Phenyl ethyl alcohol | 400 |
| 1-citronellol | 150 |
| 1-citronellyl acetate | 10 |
| Citroflex | 90 |
| Lyrol | 80 |
| Indole | 10 |
| Husk RI | 5 |
| 6-decalactone | 10 |
| 6-methoxy-2,6-dimethylheptanal | 10 |
| 6-methoxy-2,6-dimethylheptanol | 5 |
| | 1,000 |

A second composition formulated on an identical basis with the exception that the last two ingredients of the above formulation, the methoxy heptanal and the heptanol were replaced with identical quantities of 6-hydroxy-2,6-dimethylheptanal and 6-hydroxy-2,6-dimethylheptanol. This second composition possessed an odour having a much stronger fresh floral muguet lift as compared to the first.

What we claim is:

1. A perfume composition consisting essentially of perfume components comprising perfume component (i) selected from the compounds having the formula

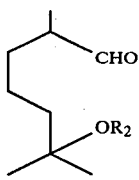

wherein $R_2$ is an alkyl group having from 1 to 4 carbon atoms, and perfume component (ii) which contains at least one odoriferous compound selected from the group consisting of 2,6 dimethyl 2 alkoxy octan-7-ols, vetivert oil, vetiverol, vetiveryl acetate, guaiac wood oil, guaiac wood acetate, coumarin, musk ketone, lauric aldehyde, benzyl acetate, dimethyl benzyl carbinol, dimethyl benzyl carbinyl acetate, rose absolute, jasmin absolute, ionones, iso-nonyl acetate, methyl phenyl acetate, styrallyl acetate, β-phenyl ethanol, citronellol, citronellal, geranium oil, geraniol, linalool, nerol, lavandin oil, linalyl acetate, patchouli oil, petitgrain oil, bergamot oil, heliotropin, ethylene brassylate, undecyl aldehyde, cinnamaldehyde, benzyl salicylate, cinnamyl alcohol, clove bud oil, bay oil, nutmeg oil, pimento berry oil, terpineol, ylang oil, benzyl benzoate, sandalwood oil, clary sage oil, amyl salicylate, labdanum resin, methyl ionones, dihydromyrcenol, orange oil, vanillin, ethylvanillin, olibanum resin, musk ambrette, rhodinol, mandarin oil, methyl nonyl acetaldehyde, neroli oil, cedrol, oakmoss, isovalanone, hydrogen, and alkyl groups having from 1 to 4 carbon atoms.

2. A composition according to claim 1 wherein $R_2$ is the methyl group.

3. A composition according to claim 1 containing from 0.1 to 20 parts by weight of said component (i).

4. A composition according to claim 3 wherein $R_2$ is the methyl group.

5. A composition according to claim 3 wherein said component (ii) contains odoriferous compound selected from the group consisting of linalool, citronellol, geraniol, phenylethyl alcohol, terpineol and hydroxy citronellal and methoxy citronellal.

6. A composition according to claim 1 wherein said component (i) comprises a mixture of at least one compound of the formula

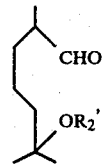

and at least one compound of the formula

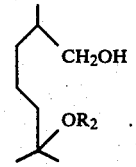

7. A composition according to claim 6 wherein said mixture contains at least 50% by weight of said aldehyde.

* * * * *